(12) United States Patent
Lonero et al.

(10) Patent No.: US 8,265,446 B2
(45) Date of Patent: Sep. 11, 2012

(54) KIT OF OPTICAL FIBERS FOR PERCUTANEOUS ABLATIVE TREATMENT

(75) Inventors: Francesco Lonero, Firenze (IT);
Leonardo Masotti, Firenze (IT);
Stefano Modi, Firenze (IT); Fabrizio Spezia, Firenze (IT)

(73) Assignee: ELESTA S.r.l., Calenzo, Firenze (IT)

( * ) Notice: Subject to any disclaimer, the term of this patent is extended or adjusted under 35 U.S.C. 154(b) by 438 days.

(21) Appl. No.: 12/517,724

(22) PCT Filed: Dec. 3, 2007

(86) PCT No.: PCT/IT2007/000839
§ 371 (c)(1),
(2), (4) Date: Aug. 24, 2009

(87) PCT Pub. No.: WO2008/068789
PCT Pub. Date: Jun. 12, 2008

(65) Prior Publication Data
US 2010/0069899 A1    Mar. 18, 2010

(30) Foreign Application Priority Data
Dec. 5, 2006 (EP) .................................. 06425821

(51) Int. Cl.
*G02B 6/00* (2006.01)
(52) U.S. Cl. ......... 385/134; 385/135; 385/136; 385/137
(58) Field of Classification Search .................. 385/134, 385/135, 136, 137
See application file for complete search history.

(56) References Cited

U.S. PATENT DOCUMENTS

| | | | |
|---|---|---|---|
| 4,580,557 A | 4/1986 | Hertzmann | |
| 4,722,337 A | 2/1988 | Losch et al. | |
| 5,125,058 A | 6/1992 | Tenerz et al. | |
| 5,848,209 A | 12/1998 | Evans et al. | |
| 5,865,833 A | 2/1999 | Daikuzono | |
| 6,106,473 A | 8/2000 | Violante et al. | |
| 6,231,568 B1* | 5/2001 | Loeb et al. | 606/15 |
| 6,829,427 B1 | 12/2004 | Becker | |
| 2002/0064328 A1 | 5/2002 | Neuberger et al. | |
| 2005/0203497 A1* | 9/2005 | Speeg et al. | 606/15 |
| 2006/0095095 A1 | 5/2006 | Cao | |

FOREIGN PATENT DOCUMENTS

| | | |
|---|---|---|
| DE | 89 07 461 | 10/1989 |
| DE | 200 03 349 U1 | 6/2000 |
| DE | 100 09 004 A1 | 10/2001 |
| EP | 0 801 928 | 10/1997 |
| EP | 1 428 482 | 6/2004 |
| EP | 1 574 176 | 9/2005 |
| GB | WO 98/18387 | 5/1998 |
| GB | 2 343 845 | 5/2000 |
| IT | WO 98/24513 | 6/1998 |
| IT | WO 2005/033738 | 4/2005 |
| WO | WO 99/15237 | 4/1999 |

* cited by examiner

*Primary Examiner* — Jennifer Doan
(74) *Attorney, Agent, or Firm* — McGlew and Tuttle, P.C.

(57) ABSTRACT

The kit of optical fibers for percutaneous ablative treatment, comprises at least two optical fibers (5), each of which is equipped; at a first end with a connector (5A) to a laser source (7); and in proximity to a second end with a device (5B) for constraining to a pervious needle (9). The kit comprises a coding system that characterizes one fiber with respect to the other, allowing said fibers to be distinguished from one another.

27 Claims, 6 Drawing Sheets

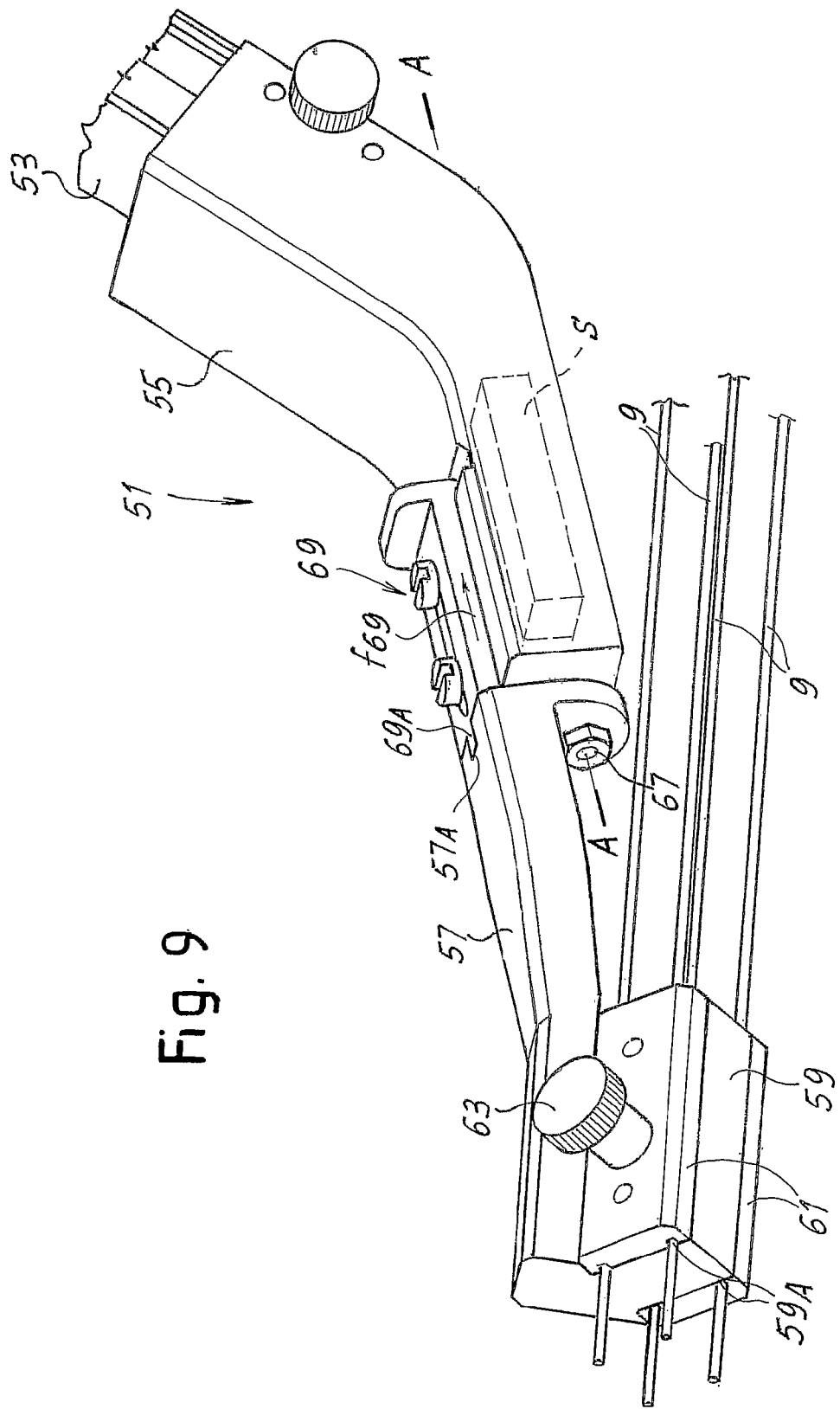

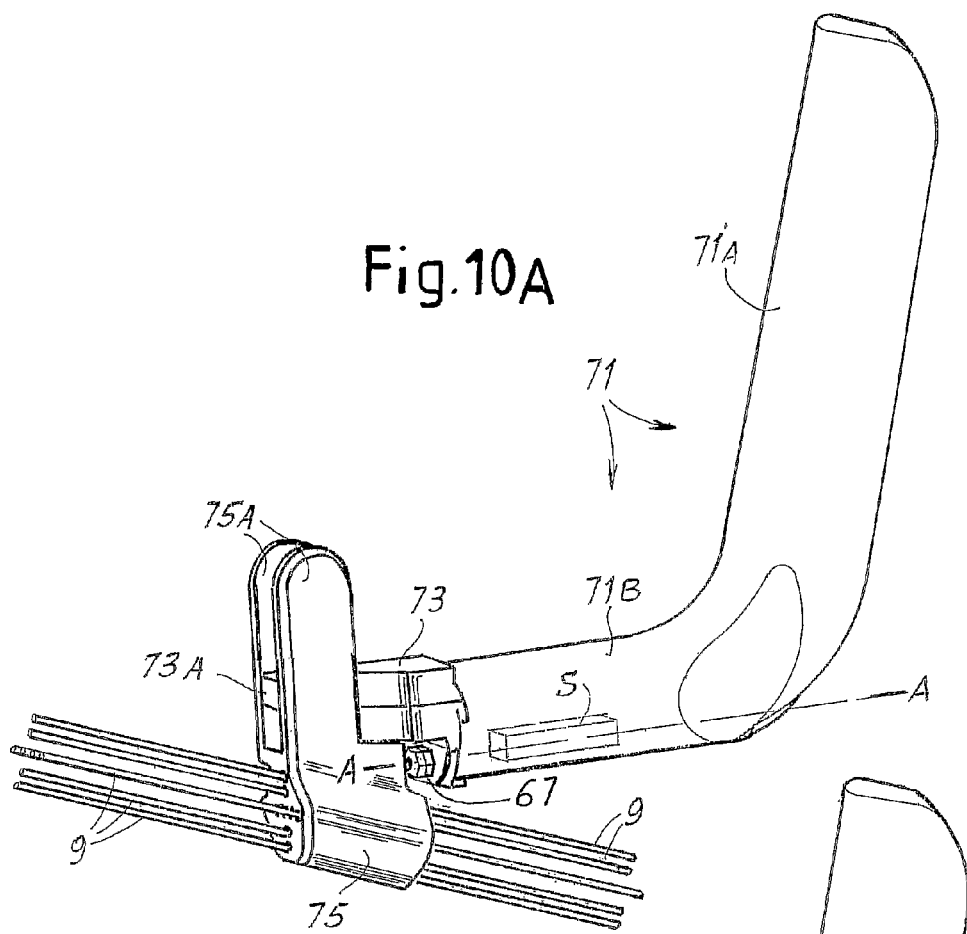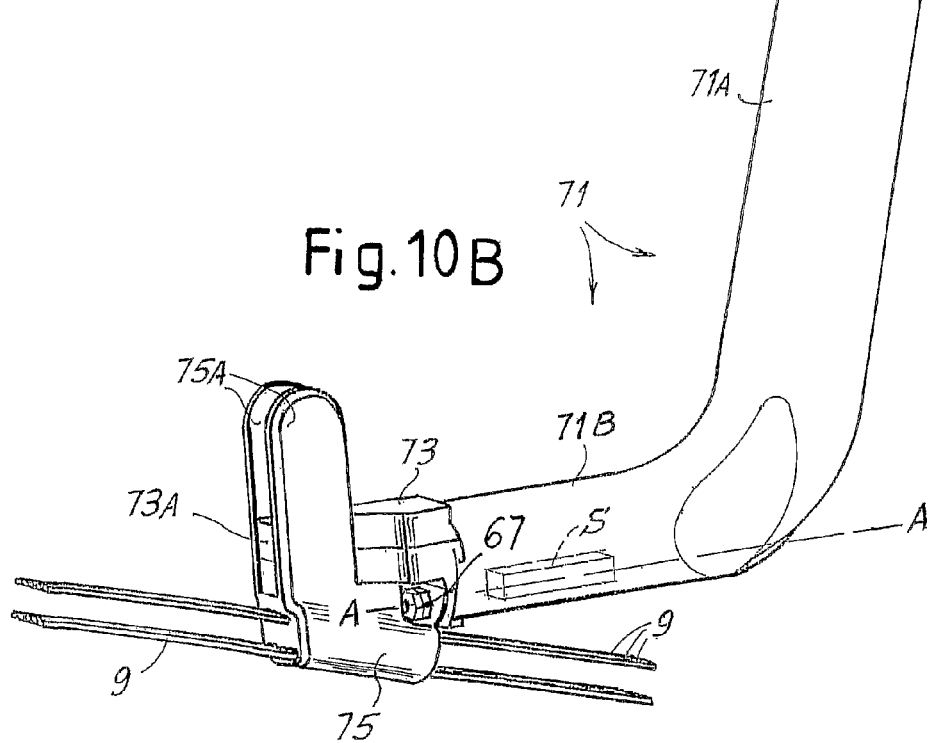

KIT OF OPTICAL FIBERS FOR PERCUTANEOUS ABLATIVE TREATMENT

TECHNICAL FIELD

The present invention relates to the field of surgical instruments and, more specifically, relates to devices, instruments and accessories for percutaneous ablative treatment performed with laser energy conveyed by means of optical fibers into tissues inside the body of the patient through pervious needles or cannulae.

PRIOR ART

Echo-guided percutaneous ablative treatment of tissue using laser generally takes place through the use of thin optical fibers (200-400 μm) which, connected to laser sources of a suitable wavelength (one of the most frequently used, although obviously not the only one, in the medical surgery field is the neodymium—Nd:YAG 1064 nm laser), are inserted in the organ to be treated through thin needles (typically with a diameter of less than 1 mm) normally used for taking cytological samples, which are positioned with the aid of ultrasound. Laser instruments allow several fibers to be connected and supplied simultaneously with energy; the resulting thermal effect, in terms of volume of necrotized tissue, is considerably greater than the sum of the thermal effects of the sources used individually. For this reason, the use of at least two fibers is very frequent, if not essential, in order to obtain appreciable results.

Some critical and determining factors for correct and effective application of the method are intrinsic in the materials described above. The needle should have characteristics of marked echogenicity to make echo-guided positioning with low traumaticity easier (thin, tip with multiple sharpening and acute angle). Enhanced echogenicity cannot be obtained by mechanically machining the outside of the cannula as this could be the source of seeding when treating neoplastic diseases; intrinsically echo-reflecting alloys or treatments that do not in any way increase the roughness or unevenness of the outer surface of the needle could be used. The tip of the fiber, which can be of the flat or machined type (conical or provided with diffuser end), must be capable of projecting from the tip of the needle by a pre-established length, which must not be exceedable for obvious safety reasons, and which can vary as a function of the organ to be treated: for example, for ablative treatment of benign thyroid nodules 5 mm are used, while 10 mm are used for the treatment of liver tumors.

Projection of the tip of the fiber from the tip of the needle is essential for correct emission of energy from the laser without interference with the metal of the cannula: otherwise, this would suffer a very significant temperature increase. To obtain this "adjustment" of the degree by which the fiber projects from the tip of the needle common torquers used in angioplasty are currently utilized. These are tightened around the fiber in the position in which it rests against the needle cone, after operations to measure the correct portion of fiber projecting from the tip of the needle, performed during the preparatory phase of surgery for each fiber-needle pair. The need to use several fibers simultaneously for effective treatment, above all in relation to volume, shape and position of the mass of tissue to be ablated, poses the problem of allowing emission of energy differentiated for each fiber or, at least, of allowing the supply for each fiber to be cut off independently.

Needles with marked characteristics of echogenicity for the purposes discussed above are known, for example, from U.S. Pat. No. 6,106,473, which describes a system for coating the needle to increase the echogenicity thereof. U.S. Pat. No. 5,865,833 describes a device for ablative laser treatment in particular to remove tumoral tissues or to treat herniated discs, wherein the needles have a surface treatment to increase the echogenicity thereof.

WO-A-9824513 describes a needle with a connector for passage of multiple optical fibers, also in this case for percutaneous treatment of tumoral tissues.

U.S. Pat. Nos. 4,722,337, 5,848,209 and 6,829,427 describe optical fibers for conveying laser radiation from a source towards an end of the fiber. These patents describe fibers having a connector equipped with electronics which allow identification of the fiber by the control unit of the laser source once the connection between fiber and source has been made.

U.S. Pat. No. 4,580,557 describes a laser system for surgical treatment by means of conveying laser radiation through optical fibers. The device allows connection of a plurality of optical fibers to the source.

US-A-2002/0064328 describes a system for connecting a cannula needle and an optical fiber, with a torquer used to lock the fiber once the position thereof has been adjusted with respect to the cannula needle.

OBJECT AND SUMMARY OF THE INVENTION

As indicated above, in percutaneous ablative treatments there is the need to modify operation of each fiber of a plurality of fibers used simultaneously in the treatment of a tissue area. For example, it may be necessary to vary the quantity of energy conveyed through a specific fiber during treatment, or also to promptly cut off the energy being conveyed through a specific fiber, while the surrounding fibers continue to operate. Moreover, it may be necessary to move the position of a needle and of the relative fiber with respect to the treated tissue, without moving the other fibers.

An object of the invention is to produce a kit of fibers which simplifies these operations.

For this purpose, according to a possible embodiment the invention provides for a kit of optical fibers for percutaneous ablative treatment comprising at least two optical fibers, each of which is equipped with a connector to a laser source and, in proximity to the distal end of the fiber (from which the laser radiation is emitted), with a device for constraining to a pervious needle or cannula. According to the invention, the fibers of the kit are characterized by a coding system which allows one fiber to be characterized, i.e. distinguished, with respect to the other. This allows the operator to act more promptly, when the operating conditions of each fiber require to be modified, as the various fibers can be more easily identified.

For example, when it is necessary to cut off the supply of energy being conveyed through one of the various fibers inserted in the tissue being treated, the coding system allows the operator to more promptly identify the connector of the fiber to be deactivated, allowing it, for example, to be simply disconnected from the laser source by removing the connector from the equipment or, preferably, interacting with a user interface that cuts off the supply after activation of controls, e.g. pressing keys with the same coding system.

In a possible embodiment, the energy supplied through the fibers can be controlled separately for each fiber, as total quantity, as power value and as law of supply through time (on for certain intervals and off for others). This method of controlling supply through the individual fibers can be facilitated by making identification of the fibers easier through the use of a kit according to the invention. However, a controlled supply method of this type can also be implemented with other types of needles and/or fibers and relative kits.

Therefore, according to one aspect of the present invention, a method of managing the supply of laser energy through a laser fiber guided in a pervious needle or cannula is provided, wherein the energy injected into the fiber is controlled as total value and/or as variation of the supply as a function of time. According to a further development of the invention, a method is provided for introducing laser energy through a plurality of light guides, such as, in particular, a plurality of optical fibers, guided in corresponding pervious needles, wherein at least one parameter of the energy supplied through each light guide or optical fiber (for example, total energy, the law of supply through time or the like) is controlled separately from the energy supplied through the other optical fibers or light guides.

Within the scope of the present description and of the appended claims, the term needle, pervious needle, cannula or cannula needle is intended generically as the element which, when inserted in the body of the patient, makes it possible to reach the position where the end of the fiber, through which the laser radiation is emitted, must be positioned. The term needle or pervious needle must therefore also be intended as a synonym of cannula or cannula needle.

In a possible embodiment, the coding system that characterizes the kit of fibers comprises at least a first coding element coupled with the corresponding device for constraining each fiber to a respective needle or cannula. This coding element can, for example, comprise a number.

However, marking with a number the device for constraining the fiber to the needle can cause some limitations, as, according to the position in which the fiber is located during the operation, the number or code marked thereon may not be instantly visible. Therefore, according to a preferred embodiment of the invention, this first coding element associated with the device for constraining each fiber is preferably constituted by a specific color. In other words, the various fibers of the kit are each characterized by a device for constraining to the respective needle having at least a colored area so that a plurality of fibers of the kit have different colors to one another.

In a further embodiment of the invention, each fiber is characterized by a second coding element combined to the corresponding connector, with which the fiber is connected to the laser source. In this way, each fiber has a first coding element associated with the device for constraining to the needle and a second coding element associated with the connector to connect the fiber to the source. Preferably, the first and the second coding element are the same as each other or, in any case, easily couplable with each other. For example, they can be constituted for each fiber by the same number, figure, letter or other graphical element. The kit could, for example, contain fibers numbered from 1 to N, where the number is marked both on the device for constraining to the needle and on the connector to the source.

Nonetheless, for the reasons indicated above, the second coding element is also preferably an element of chromatic type, i.e. a color. In this case, preferably both the connector and the device for constraining to the needle of each fiber will be characterized by a color that will preferably be the same for these two components of the fiber and for a specific number of fibers of the kit each fiber will have connector and device for constraining to the needle in different colors for easy identification.

According to a preferred embodiment of the invention, the kit also has a plurality of needles. These needles can be the same as or different from one another. For example, a specific kit can be dedicated to treating a specific organ, or the same kit can have series of needles for treating different organs. For example, one kit can have needles all of the same length for treating hepatic tumors, while another kit can have needles of a different type for treating the thyroid.

In a preferred embodiment of the invention the needles of the kit or at least some needles of the kit will also be characterized by a code that allows one needle to be distinguished from the other and allows each needle to be coupled with a corresponding fiber. For example, the cone of the needle that cooperates with the constraining device present on the fiber can be equipped with a graphic element (number or letter) or preferably with a chromatic element (i.e. a color) corresponding to the one marked on the respective fiber.

According to an improved embodiment of the invention, the needles of the kit have characteristics of echogenicity designed specifically to allow more effective identification through ultrasound imaging. In this case, according to an improvement of the invention, the needles or at least some of the needles of the kit can be coded using characteristics of echogenicity differing from one another to distinguish one needle from the other in the ultrasound image. For example, utilizing one of the known techniques for providing needles with specific characteristics of echogenicity, according to one embodiment of the invention the needles of the kit are provided with bands or strips with greater echogenicity obtained, for example, by coating. In this way not only can the operator distinguish one fiber from the other by the coding of the device for constraining to the needle and of the connector to the laser source, but can also identify which needle corresponds to which fiber by observing the ultrasound image. For example, needles that can be distinguished on the ultrasound image due to the presence of a different number of bands of greater echogenicity can be associated with two fibers characterized by different colors (black and white). The first needle, associated with the white fiber, could have a single band with more marked echogenicity, while the second needle could have two of said bands. In the preparatory phase of the surgical operation, the operator will take note of the combination of the color of the fiber with the echogenic characteristic of the respective needle, so that he can observe the progress of the ablative surgery on the ultrasound image identifying the two needles on said image and therefore, in case of need, being able to identify on said image which of the two needles requires an operation to reduce/increase the laser emission, to be removed, moved or the like. In this case immediate action can be taken on the corresponding fiber by identifying it by means of the respective color.

With modern ultrasound systems (see for example WO-A-2005/033738) it is also possible for the control unit of the ultrasound device to identify and distinguish one needle with respect to the other by means of the different characteristics of echogenicity of the needles simultaneously inserted in the area to be treated and visible on the ultrasound image. The ultrasound device can be programmed to superimpose a false color image over the ultrasound image, which allows each colored needle to appear on the monitor or the ultrasound device with a color corresponding to the color characterizing the fiber connected to the needle. This makes the surgical operation even simpler and more reliable, as the operator can act on the operating conditions of each needle, identifying it through the false color assigned thereto by the ultrasound device and corresponding to the color with which the respective fiber is coded.

The fibers can have connectors equipped with electronics which, at the moment of coupling the fiber with the source, connect to the control electronics of the laser source. This allows the machine to automatically identify the type of fiber connected and also to distinguish one fiber from the other. For example, each color used to code one of the fibers of the kit corresponds to a datum memorized in a chip of the connector of the fiber.

When the fibers are provided with a connector with onboard electronics that allow the source to identify one fiber with respect to the other, it is possible to program the laser source so that it does not allow more than one fiber of the same color to be applied simultaneously, thereby preventing the operator from erroneously using two or more fibers that cannot be distinguished from one another.

The device for constraining the fiber to the needle can comprise a through hole inside which the fiber is inserted and from which the fiber projects by a length predetermined as a function of the length of the needle to be coupled with the fiber and of the quantity by which the fiber must project from the tip of the needle. The fiber can be bonded in the through hole so as to take a fixed position with respect to the device for constraining the fiber to the needle.

However, according to an improved embodiment of the invention, the device for constraining the fiber to the needle comprises a system for adjusting the length of the portion of fiber that can be inserted in the needle. In this case, the constraining device will be equipped or coupled with a torquer or other similar device, which allows the fiber to run through the through hole in the constraining device and be locked by means of radial tightening in the chosen position, wherein the output end of the fiber will be positioned at the required distance with respect to the device for constraining the fiber to the needle.

In a possible embodiment, the needles and the devices for constraining the fibers to the needles can be characterized, as well as by a graphic or chromatic element that distinguishes one fiber/needle pair from another fiber/needle pair, also by a different interlocking system for each fiber/needle pair, so that each fiber can only be constrained to the respective needle having the same coding element. For example, rather than using conical-shaped interfaces between constraining device and needle, pyramid-shaped constraining interfaces with a variable number of faces for each needle/fiber pair can be used.

In a possible embodiment, to facilitate preparation of the equipment before the surgical operation, the device for constraining the fiber to the corresponding needle can advantageously have a portion that is at least partially transparent and provided with a graduated scale, through which a reference mark, such as a band, trace or annular notch applied to or produced on the fiber, is visible. The reciprocal position between the constraining device and the fiber is adjusted by positioning the reference mark of the fiber on the graduated scale and subsequently locking the fiber using a torquer or other similar device.

According to a further embodiment, the kit can also comprise a guide for one or more needles. This guide can for example be constrained to or constrainable to an ultrasound probe or to a handpiece with a coupling that allows the position of the guide, and therefore of the needles inserted therein, to be adjustable with respect to the position of the probe.

By making the needle guide movable with respect to the ultrasound probe it becomes possible to alternately take several needles to the plane on which the ultrasonic waves generated by the probe propagate, rotating the position of the probe with respect to the guide once the needles fixed inside the guide have been inserted into the body of the patient. This makes it possible to observe several needles on the ultrasound image which, as a rule, are not and cannot be positioned simultaneously on the plane along which the ultrasound waves propagate.

A handpiece of this type, which has a support for the needle guide that is movable with respect to the position of the ultrasound probe of the handpiece, can advantageously also be utilized separately from the other elements of the kit described above. The handpiece with the movable support for the needle guide constitutes an improvement, the advantages of which can also be exploited separately from the coding of the needles and of the fibers, provided for simpler and more immediate identification of the various fibers and of the various needles during the surgical operation. In other words, the handpiece with the support adjustable in position on which the needle guide is positioned can be utilized with uncoded needles and fibers or, in any case, configured differently to the description above.

BRIEF DESCRIPTION OF THE DRAWINGS

The invention will be better understood by following the description and accompanying drawing, which shows non-limiting practical embodiments of the invention. More specifically, in the drawing:

FIGS. 9, 10A, 10B, 11 show embodiments of a handpiece with a needle guide movable with respect to the ultrasound probe contained in the handpiece.

DETAILED DESCRIPTION OF EMBODIMENTS OF THE INVENTION

Figure 1:
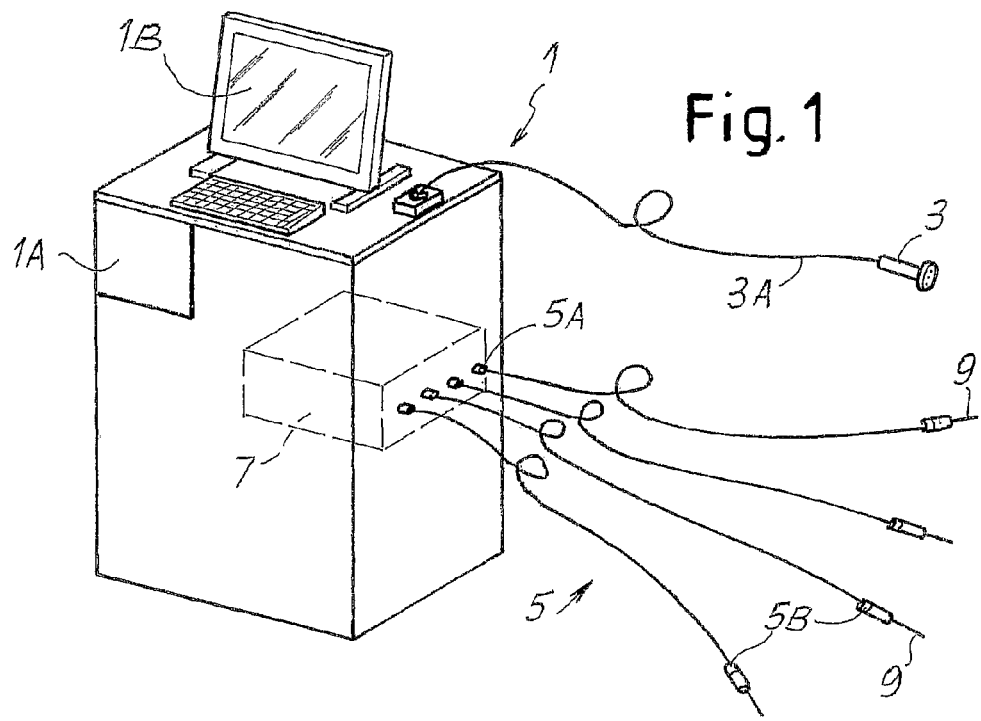
FIG. 1 very schematically shows ultrasound laser equipment to which a kit according to the invention can be applied.

FIG. 1 very schematically indicates an ultrasound laser equipment 1 comprising at least one ultrasound probe 3 connected by means of a cable 3A to the equipment and a series of optical fibers 5, each provided with a connector 5A for connection to a laser source, indicated schematically with 7, belonging to the equipment 1. Each optical fiber 5 comprises, at the opposite end thereof with respect to the connector 5A, a device 5B for constraining to a corresponding pervious needle or cannula 9.

Figure 2:
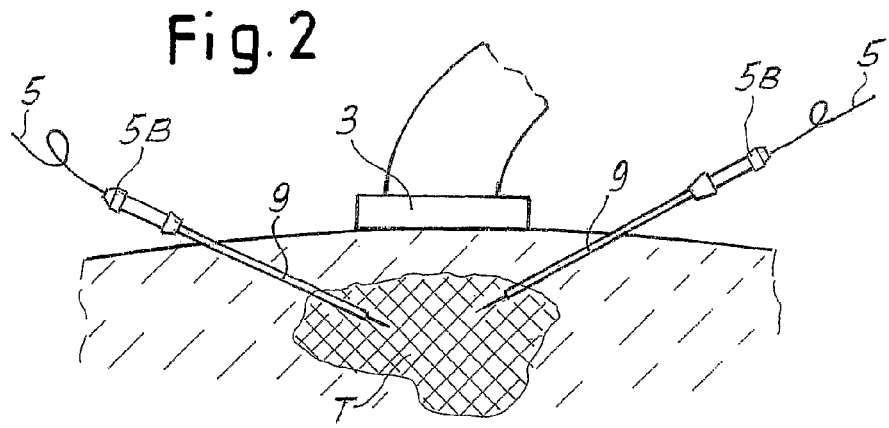
FIG. 2 very schematically shows an area in which a percutaneous ablation is performed by means of a plurality of fibers of a kit according to the invention under the control of an ultrasound probe.

FIG. 2 very schematically indicates how several needles or cannulae 9 (in the example two pervious needles 9) can be inserted in the mass of tissue T to be treated, e.g. a tumoral tissue, to convey therein the laser radiation guided through the respective optical fibers 5 connected to the needles 9 by means of the corresponding constraining devices 5B.

Figure 2A:
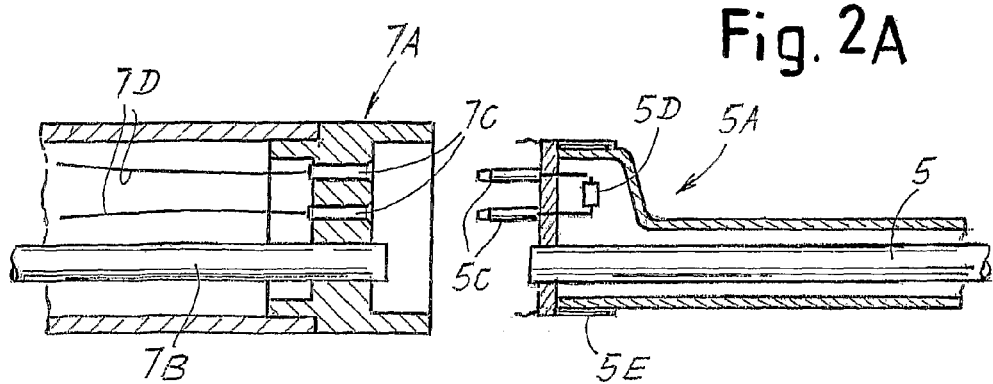
FIG. 2A shows a diagram of a connector of the fiber to the laser source.

In a way known per se, the connector 5A of the fibers 5 can comprise electronics that allow the control unit 1A of the ultrasound-laser apparatus or device 1 to identify each fiber 5 connected to the laser source 7. FIG. 2A schematically shows the fiber 5 with the connector thereof towards an interface 7A of the laser source, where 7B indicates a light guide that conveys towards the element 7A the radiation coming from the actual laser, while 7C indicates electrical connectors cooperating with pins 5C of the connector 5A of the optical fiber 5. The reference 5D schematically indicates an electronic component that can contain the information required in order for the control unit, connected by means of the leads 7D to the connectors 7C, to identify the optical fiber 5.

It is thus possible to characterize each fiber 5 of a kit through information stored in the electronics 5D, so that once the various fibers 5 are connected to the ultrasound laser equipment 1, the control unit 1A can identify them and, if necessary, prevent more than one fiber characterized by the same code from being connected simultaneously to the source.

According to a possible embodiment, the connectors 5A of a kit of fibers 5 can all also be characterized by a coding element visible externally, preferably constituted by a color which can, for example, be marked on a band 5E that surrounds the connector 5A.

At the opposite end with respect to the connector 5A, each fiber 5 of the kit has a constraining device 5B from connection to the respective needle 9. According to an advantageous embodiment of the invention, the constraining device 5B can have a coding element preferably the same as the one 5E characterizing the connector 5A. Preferably, the constraining device 5B has a different color from fiber to fiber and, for each fiber, the same as the color characterizing the corresponding connector 5A.

According to an advantageous embodiment, each needle 9 has an interface for connection to the fiber, hereinafter indicated as cone 9A (FIGS. 3 to 8). Preferably, the interface or cone 9A is also characterized by a coding element which can, for example, be constituted by specific coloring. Preferably, the color of the cone 9A is the same as the color of the constraining device 5B and of the connector 5A of the fiber to which the specific needle 9 must be interfaced.

In this way, in a specific kit comprising a certain number of needles and fibers, it will be possible to couple each needle 9 with one and only one of the various fibers 5, and each fiber/needle pair will be characterized by a connector 5A, a device 5B for constraining to the needle 9 and a cone 9A of the needle 9 of the same color.

Observing the surgical operation on the monitor 1B of the laser-ultrasound equipment 1, the operator can check whether, for one or other of the needles 9, it is necessary to increase or decrease the quantity of energy, deactivate the needle, modify the position thereof, etc. On the basis of the color characterizing the various components of the fiber/needle pair, the operator can act promptly without confusing one needle with the other and one fiber with the other. For example, if one of the needles 9 requires to be immediately deactivated, the operator can immediately trace, by means of its color, the connector 5A to be removed from the source or, in any case, to be deactivated so that introduction of energy through that specific needle ceases forthwith.

Figure 3:
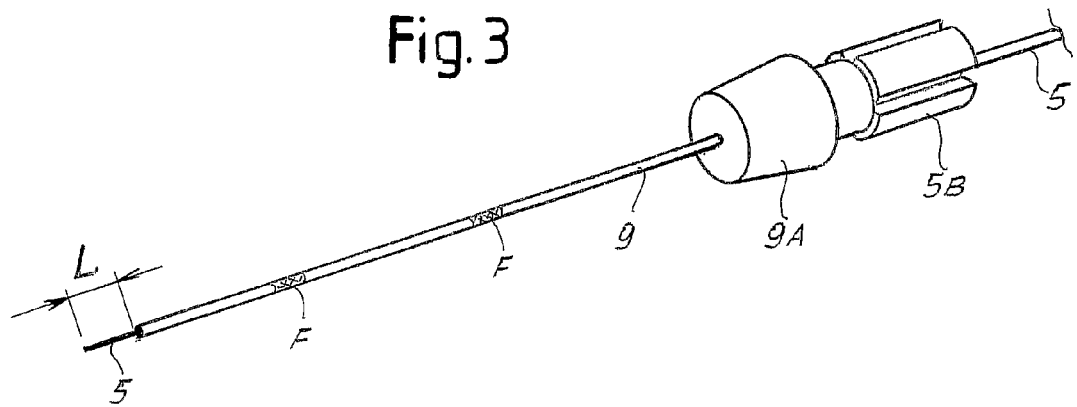
FIG. 3 shows a first embodiment of a needle or cannula with the respective fiber coupled therewith by means of a fiber/needle constraining device.
Figure 4:
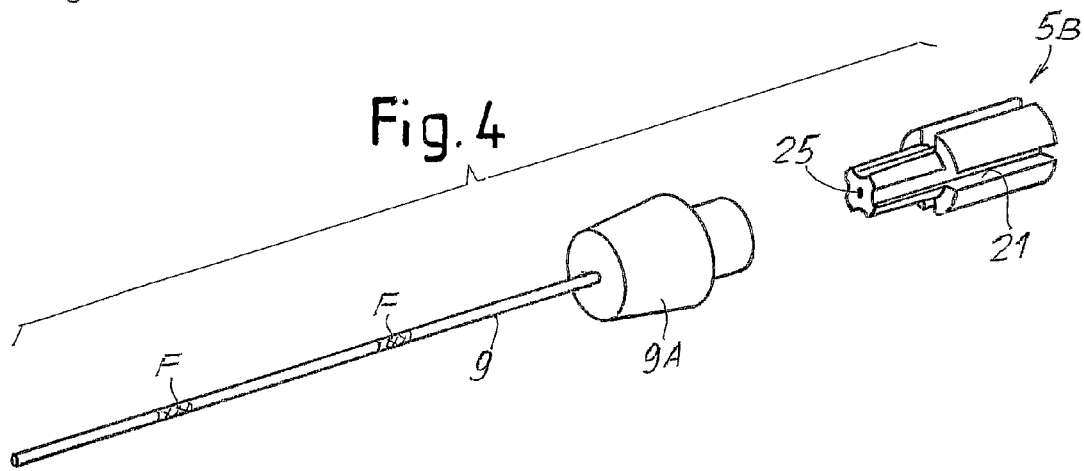
FIG. 4 shows a view of the two components, needle and device for constraining the fiber to the needle, of the device in FIG. 3.
Figure 5:
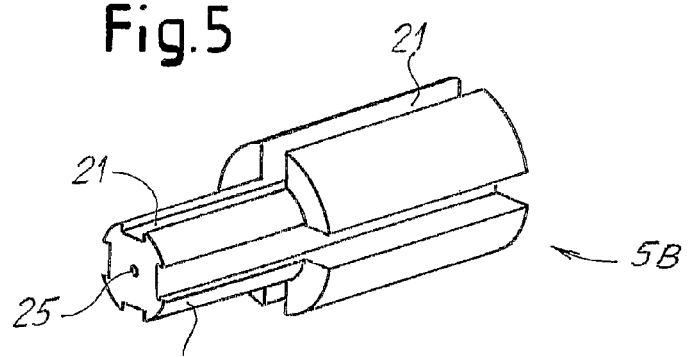
FIG. 5 shows an enlargement of the constraining device in FIG. 4.

As can be observed in FIGS. 3, 4 and 5, according to a first embodiment of the invention, the device 5B constraining the fiber 5 to the respective needle 9 has a substantially cylindrical body with longitudinal grooves 21, which also extend in a portion of lesser diameter 23 of the constraining device 5B. The portion 23 is inserted with slight interference in a corresponding seat (not shown) inside the cone or interface 9A. The grooves 21 place the inside of the needle 9 in communication with the external environment and allow the discharge of vapors or liquids that can generate inside the treated tissue T due to the supply of energy that vaporizes the tissue. The diameter of the fiber 5 that passes through the needle 9 is substantially smaller than the diameter of the inner hole of said needle 9, so that said vapors or other products of vaporization of the tissues T can be discharged from the body of the patient passing through the empty volume between the external surface of the fiber 5 and the internal surface of the cannula or needle 9 and along the grooves 21.

Passing through the constraining device 5 is a through hole 25, through which the fiber 5 passes. This fiber can be fixed, e.g. by means of a suitable glue, in a fixed position inside the through hole 25, so that the distance between the constraining device 5B and the end edge of the fiber 5 from which the laser radiation guided inside the fiber is irradiated is fixed. Consequently, in the assembled layout in FIG. 3, the fiber 5 projects by a fixed and non-adjustable length L from the distal end of the cannula or needle 9.

The conformation of the portion 23 of the constraining element or device 5B is preferably slightly tapered to couple with slight interference with the corresponding seat of the cone 9A of the needle 9. The geometrical shape of the portion 23 and of the seat in which it is inserted in the cone 9A can be variable from fiber to fiber to prevent reciprocal coupling between a needle 9 and a fiber 5 not corresponding to said needle. Nonetheless, color coding of the cone or interface 9A of the needle and of the constraining device 5B make the kit sufficiently safe to use, so that different shaping of the reciprocal fiber/needle coupling in order to avoid erroneous coupling is unnecessary.

According to an advantageous and preferred embodiment, the needles 9 of the kit can have characteristics of echogenicity that vary from needle to needle. In the example in FIGS. 3 and 4, the needle 9 is marked with bands F (two in number on this needle) produced, for example, with a coating that locally alters the reflection characteristics of the ultrasonic waves coming from the ultrasound probe 3. By equipping the various needles of the same kit with bands F in variable numbers and/or positions and/or dimensions it is possible to identify the various needles on the ultrasound image shown on the monitor 1B. Modern systems can also allow automatic identification of the needles and, if necessary, superimposing of a false color on the image of each needle, with a chromatic characteristic the same as the one characterizing the cone 9A, the constraining device 5B and the connector 5A of the fibers.

Figure 6:
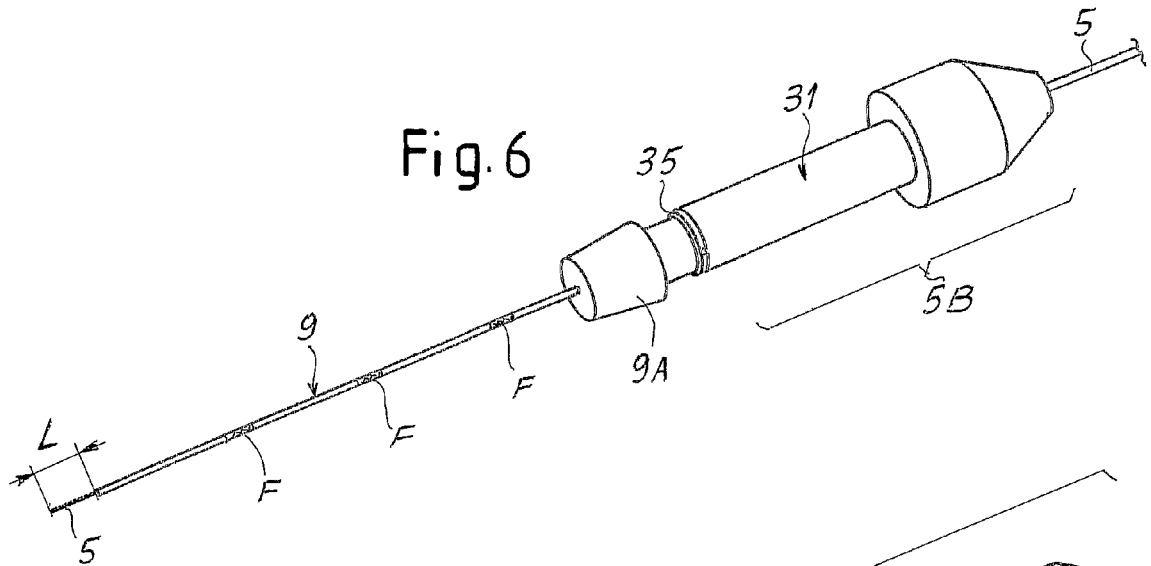
FIGS. 6, 7 and 8 show view analogous to those in FIGS. 3, 4 and 5 in a different embodiment of the invention.
Figure 7:
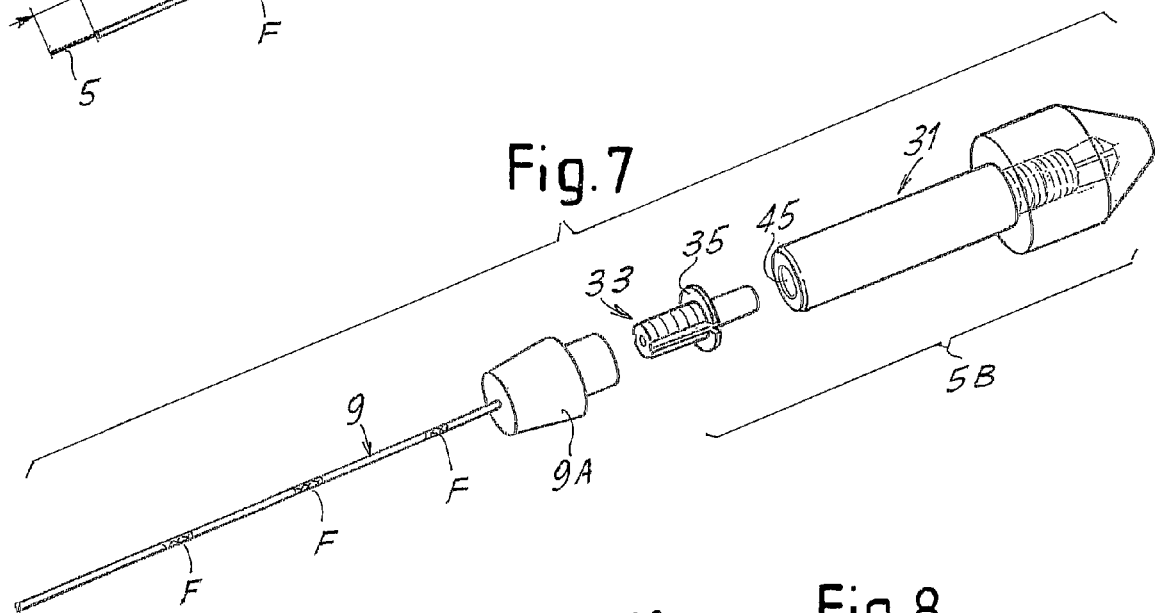
Figure 8:
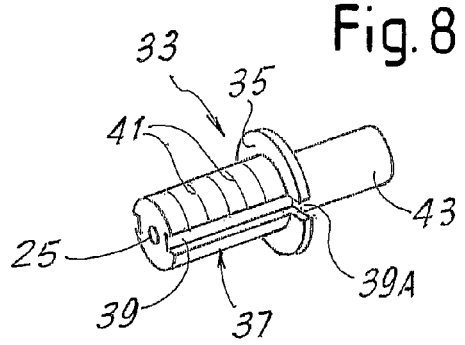

FIGS. 6, 7, and 8 show a different embodiment of the device 5B for constraining the fiber 5 to the respective needle 9. The same numbers indicate the same or equivalent parts to those illustrated in FIGS. 3, 4 and 5.

In this embodiment, the constraining device 5B is formed of two components and more specifically of a locking member 31, such as a torquer, which allows the fiber to be locked in an adjustable axial position, and of an element 33 for coupling with the cone 9A of the needle 9.

In an advantageous embodiment, the constraining element 33 comprises a flange 35 extending on one side of which is a portion 37 for coupling with the cone 9A of the needle, substantially equivalent to the portion 23 of the constraining device 5B illustrated in FIGS. 3, 4 and 5. This portion 37 has grooves 39 equivalent to and having the same function as the grooves 21 of the device 5B of FIGS. 3, 4 and 5. The grooves 39 correspond to slots 39A produced in the flange 35.

According to an advantageous embodiment, a graduated scale 41 (FIG. 8) is produced on the portion 37, and said portion 37 is advantageously formed at least in part of a transparent or translucent plastic material, which allows the fiber passing through the central hole 25 to be viewed through the depth of the material. The fiber 5 is advantageously characterized by the presence of a reference mark, such as a dark annular band on the outer surface of the fiber. The reference mark can be taken to the desired position along the scale 41. In this case, it is thus possible to modify the length of the section of fiber projecting from the constraining device 5B and consequently the length L by which the fiber 5 projects from the distal end of the needle or cannula 9.

The torquer or other locking member of the fiber, indicated schematically with 31, allows the grip on the fiber 5 to be slackened so that it can be moved to the desired axial position determined on the scale 41. After reaching this position, the torquer 31 is tightened again to lock the fiber.

On the opposite side of the flange 35 with respect to the side on which the portion 37 is produced, is a tang 43 which is inserted in a seat 45 of the torquer or other locking device or member of the fiber 31. Coupling between the tang 43 and the seat 45 can be a stable and irreversible coupling, obtained for example by bonding, or an interlocking coupling.

In the example illustrated in FIGS. 6 and 7, bands F with different echogenicity with respect to the remaining surface of the needle 9 are once again produced on the cannula or pervious needle 9. In this case, these bands are marked, by way of example in the number of three, to show how it is possible to characterize and distinguish the various needles 9 in the same kit from one another, thereby making them distinguishable on the ultrasound image.

Hereunder further accessories will be described, which can be included in the kit described above, but which could also be utilized separately from the remaining aforesaid characteristics of said kit.

In substance, these are handpieces containing an ultrasound probe and comprising a guide for inserting one or more needles or cannulae through which the optical fibers are made to penetrate the body of the patient until reaching the tissue to be treated under the control of the ultrasound probe.

The handpieces illustrated in FIGS. 9, 10A, 10B, 11 are particularly suitable to treat benign thyroid nodules, but not exclusively dedicated to this use. In fact, they can also be applied advantageously in different uses, each time it is helpful or necessary to modify the reciprocal position between the ultrasound probe and the needle or cannula guide.

With initial reference to FIG. 9, the handpiece indicated with 51 comprises a portion 53 which can be formed by a conventional handpiece contained inside which, in a position indicated schematically with S, is an ultrasound probe of a type known per se.

According to an advantageous embodiment, to the element 53 an accessory 55 is applied, which forms part of the handpiece 51 and constrained to which is a support 57 for a guide 59 of needles or cannulae 9 which, in this example, are provided in the number of four, but which may vary in number according to the form of the guide 59. In this example, the needles 9 are received in seats 59A produced in the guide 59 by means of plates 61 locked by means of a knob 63. The plates can be separated to allow effective sterilization thereof. It would also be possible to constrain the needles 9 to the guide 59 in a different way. The needles can be housed in the seats 59A with slight interference which in any case allows axial movement and retaining through friction even when the guide 59 is closed by means of the plates 61.

The support 57 is constrained to the accessory 55 so that the two components 55, 57 can rotate about an axis of rotation or oscillation A-A coincident with the axis of a screw 67 or other element for reciprocal connection of the components 55 and 57. In this way the position of the needles 9 can be modified with respect to the emission plane of the ultrasonic waves by the probe S and therefore one or other of the various needles 9 inserted in the guide 59 can be taken to lie on the plane of the image generated by the probe S.

The numeral 69 generically indicates a device to block reciprocal rotation of the components 55 and 57. By means of a movement according to the arrow f69 it is possible to release a tooth 69A, provided on the device, from a notch 57A provided on the support 57. In this way the handpiece 55 can rotate with respect to the support 57 during any phase of the operation, when, for example, the needles 9 are already inserted in the tissue to be treated. In this way even when the needles 9 are not all located in the propagation plane of the ultrasonic waves generated by the probe S, by means of rotation about the axis A-A of the handpiece 55, it is possible each time to bring the various needles 9 back into the ultrasound image and consequently check, for example, the insertion position in the tissue and/or the progress of the percutaneous tissue ablation process.

FIGS. 10A and 10B show a different embodiment of a handpiece having equivalent functions to those of the handpiece shown in FIG. 9. In this case the handpiece, indicated as a whole with 71, and having a handgrip 71A, houses in a portion 71B an ultrasound probe again indicated very schematically with S. Constrained to the handpiece 71, and more specifically to the portion 71B of said handpiece, is a support 73 hinged by means of a screw 75 to the handpiece 71, so that the support 73 and the handpiece 71 can rotate about the geometrical axis A-A for the same purposes illustrated with reference to FIG. 9. Constrained to the support 73 is a guide 75 for the needles 9. In this example of embodiment the guide 75 is formed on a component releasable from the support 73. FIGS. 10A and 10B show two different forms of the guide 75, as, for example, a kit with a handpiece 71 and several guides 75 differing from one another in shape, number of seats for the needles 9 and the like, can be provided.

In a possible embodiment coupling between the guide 75 and the support 73 is obtained by means of interference between a projection 73A of the support 73 and tabs 75A integral with the corresponding guide 75. An effective and quick coupling between the guide 75 and the support 73 associated with the handpiece 71 is thereby obtained. It is thus possible to easily remove the guide 75 and, for example, to replace it with another during the same surgical operation, just as it is possible to easily separate the guide 75, for example to subject it to a sterilization cycle after separating it from the handpiece 71.

A suitable elastic system can be provided to determine a stable angular position between the support 73 and the handpiece 71 in the same way to what is obtained with the device 69 in the handpiece in FIG. 9. For example, there can be provided a notch on the support 73 and a seat in the handpiece 71 with a spherule elastically stressed to project from said seat and be inserted in the notch produced in the support 73. It would also be possible to utilize on the handpiece 71 a locking device the same as the one 69 in FIG. 9.

Figure 11:
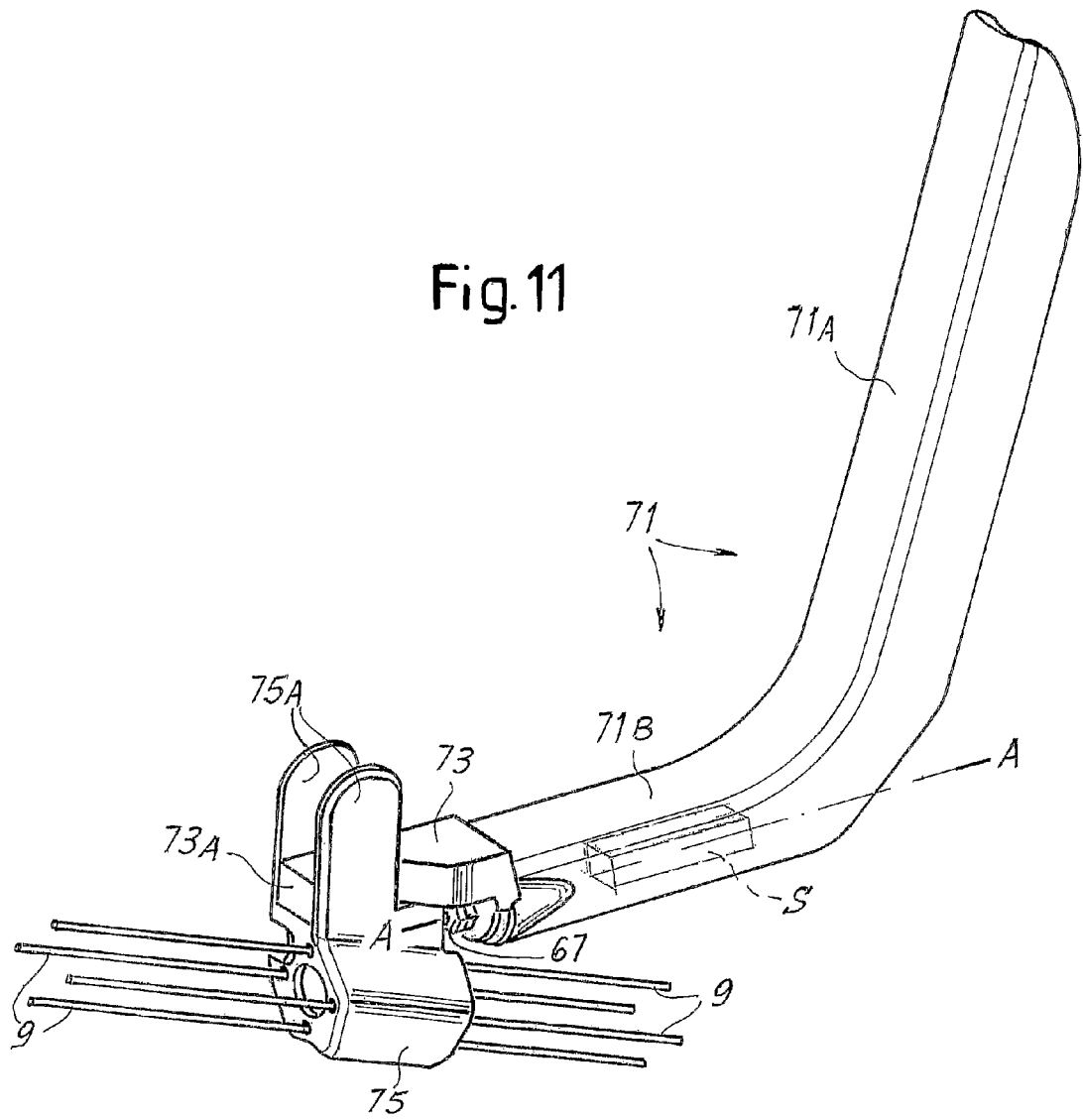

FIG. 11 shows a different embodiment of the handpiece 71. The same numbers indicate parts the same as or equivalent to those in FIGS. 10A and 10B.

In the description above reference was made to optical fibers that project by a certain degree, if necessary adjustable, from the tip of the needle, to prevent localized overheating of the needle due to the incidence of the laser energy. In a possible variant of embodiment, the laser energy can also be supplied at the tip of the needle without projection or with only limited projection of the fiber from the needle, or if necessary even with the end of the fiber remaining inside the needle. To prevent the needle from overheating, according to a possible embodiment the power supplied can be modulated or regulated appropriately. Alternatively, or in combination, by means of the needle, a liquid, such as a saline solution, can be made to circulate or introduced into the space between the inner wall of the needle or cannula and the outer wall of the fiber. This liquid can be used for localized cooling of the needle. A modest flow of biocompatible liquid, such as a saline solution, through the pervious needle carrying the fiber prevents tissue carbonization. Circulation of the liquid can be intermittent, periodically filling and emptying the cavity formed in the tissue around the needle, which is generated through contraction of the tissue containing the denatured proteins following the first phases of treatment.

Therefore, according to a particular aspect of the invention, there is also provided a method for supplying laser energy through a fiber guided in a pervious needle, wherein said pervious needle is cooled by means of feeding a liquid coolant continuously or discontinuously through said needle.

Advantageously, both in this case, and also in a configuration without introduction and/or circulation of a liquid coolant, the pervious needle can be connected to a system for aspiration of the liquids, vapors or other residues from the needle. In the case of supplying a liquid coolant, this system allows efficient cooling of the needle preventing, for example, tissue carbonization. In the case in which this cooling effect is not required, aspiration in any case facilitates removal of the products of the ablation treatment.

Therefore, a further aspect of the present invention is constituted by a method of conveying laser energy through a fiber guided in a pervious needle, wherein aspiration of a liquid coolant and/or of the residues of laser ablation caused by said energy is performed.

It is understood that the drawing only shows an example provided purely as a practical arrangement of the finding, as said finding can vary in forms and arrangement without however departing from the scope of the concept underlying the finding.

The invention claimed is:

1. A kit of optical fibers for percutaneous ablative treatment comprising:
    at least two optical fibers, each of said at least two optical fibers comprising a connector to a laser source at a first end thereof and a device for constraining a pervious needle in proximity to a second end thereof;
    a coding system that characterizes one fiber with respect to the other, allowing said fibers to be distinguished from one another, and wherein said coding system comprises for each fiber a first coding element combined to the corresponding device for constraining said fiber to the needle, wherein said devices for constraining the fibers to the needles differ in color from one another, to distinguish one fiber from the other, the color constituting said first coding element.

2. A kit as claimed in claim 1, wherein said coding system comprises for each fiber a second coding element combined to the corresponding connector.

3. A kit as claimed in claim 1, wherein said coding system comprises for each fiber a second coding element combined to the corresponding connector, said second coding element comprising a color associated to the color of the respective device for constraining the fiber to the needle, each fiber comprising a constraining device and a connector marked with substantially the same colors and differing from the colors of the other fiber or fibers.

4. A kit of optical fibers for percutaneous ablative treatment comprising:
    at least two optical fibers, each of said at least two optical fibers comprising a connector to a laser source at a first end thereof and a device for constraining a pervious needle in proximity to a second end thereof;
    a coding system that characterizes one fiber with respect to the other, allowing said fibers to be distinguished from one another, and wherein said coding system comprises for each fiber a first coding element combined to the corresponding device for constraining said fiber to the needle;
    at least two needles having characteristics differing from one another to distinguish one needle from the other, each of said needles having a coding corresponding to the coding of a respective fiber, to unequivocally couple each fiber with a respective needle corresponding thereto.

5. A kit as claimed in claim 4, wherein said needles have characteristics of echogenicity differing from one another to distinguish one needle from the other in an ultrasound image.

6. A kit as claimed in claim 4, wherein said needles comprise a member for connection to the constraining device of the fiber.

7. A kit as claimed in claim 6, wherein the members for connecting the needles to the constraining devices of the fibers have a third coding element, correlated to at least said first coding element of the corresponding fiber, to couple each needle with a respective fiber of the kit.

8. A kit as claimed in claim 7, wherein the members for connecting the needles to the constraining devices of the fibers have colors differing from one another to distinguish one needle from the other and the colors of said connection members define said third coding element and correspond to the colors of the devices for constraining the fibers to the needles.

9. A kit as claimed in claim 1, wherein the connectors of said fibers comprise electronics for identification of the fiber.

10. A kit as claimed in claim 9, wherein said electronics contain data to identify the type of fiber.

11. A kit as claimed in claim 9, wherein said electronics contain data for handling the energy supplied to said fiber by a laser source to which said fiber is connected.

12. A kit of optical fibers for percutaneous ablative treatment comprising:
    at least two optical fibers, each of said at least two optical fibers comprising a connector to a laser source at a first end thereof and a device for constraining a pervious needle in proximity to a second end thereof;
    a coding system that characterizes one fiber with respect to the other, allowing said fibers to be distinguished from one another, and wherein said coding system comprises for each fiber a first coding element combined to the corresponding device for constraining said fiber to the needle, wherein said device for constraining the fiber to the needle comprises a through hole for said fiber and a first end constrainable to said needle, a system to regulate the length of the portion of fiber insertable in said needle and a member to lock the fiber in an axially adjustable position inside the through hole, said member to lock the fiber being positioned at a second end of the constraining device, opposite the first end constrainable to the needle.

13. A kit as claimed in claim 12, wherein said device for constraining the fiber to the needle comprises an at least partially transparent portion, on which a graduated scale is marked and the fiber has a reference mark visible through said transparent portion to adjust the position of the fiber with respect to the device for constraining the needle.

14. A kit as claimed in claim 1, wherein each of said constraining devices comprises: an intermediate flange; on one side of said flange an end for connection to the needle; and on the opposite side of said flange a tang through which said fiber passes.

15. A kit of optical fibers for percutaneous ablative treatment comprising:
at least two optical fibers, each of said at least two optical fibers comprising a connector to a laser source at a first end thereof and a device for constraining a pervious needle in proximity to a second end thereof;
a coding system that characterizes one fiber with respect to the other, allowing said fibers to be distinguished from one another, and wherein said coding system comprises for each fiber a first coding element combined to the corresponding device for constraining said fiber to the needle, said device for constraining the fiber to the needle comprising a through hole for said fiber and a first end constrainable to said needle and an at least partially transparent portion, on which a graduated scale is marked and the fiber has a reference mark visible through said transparent portion to adjust the position of the fiber with respect to the device for constraining the needle, each of said constraining devices comprising an intermediate flange, on one side of said flange an end for connection to the needle, and on the opposite side of said flange a tang through which said fiber passes, said at least partially transparent portion with said graduated scale being provided on said end for connection to the needle.

16. A kit as claimed in claim 14, wherein said tang is constrained to a member to lock the fiber in an axially adjustable position inside a through hole in said constraining device.

17. A kit as claimed in claim 1, wherein each of said constraining devices comprises at least a passage for discharge of products deriving from laser ablation of tissue.

18. A kit as claimed in claim 1, further comprising at least one guide for at least one needle.

19. A kit as claimed in claim 18, wherein said guide comprises seats for a plurality of needles.

20. A kit of optical fibers for percutaneous ablative treatment comprising:
at least two optical fibers, each of said at least two optical fibers comprising a connector to a laser source at a first end thereof and a device for constraining a pervious needle in proximity to a second end thereof;
a coding system that characterizes one fiber with respect to the other, allowing said fibers to be distinguished from one another, and wherein said coding system comprises for each fiber a first coding element combined to the corresponding device for constraining said fiber to the needle;
at least one guide for at least one needle, wherein said at least one guide comprises two portions movable in relation to one another, one of said portions comprising one or more seats for passage of the needles and the other of said portions being constrainable to an ultrasound probe, the reciprocal layout of said two portions being variable to modify the relative position between ultrasound probe and needles.

21. A kit as claimed in claim 20, wherein said two portions are rotatable with respect to each other about a reciprocal axis of oscillation.

22. A kit as claimed in claim 1, further comprising a handpiece with an ultrasound probe and a support movable with respect to said probe, to which a guide for one or more needles is reversibly coupled.

23. A kit of optical fibers for percutaneous ablative treatment comprising at least two optical fibers, each of which is equipped: at a first end with a connector to a laser source and, in proximity to a second end with a device for constraining to a pervious needle, wherein: a coding system is provided for individually characterizing one fiber with respect to the other, allowing said fibers to be distinguished from one another; and comprising at least two needles having echogenicity characteristics differing from one another to distinguish one needle from the other in an ultrasound image.

24. A kit of optical fibers for percutaneous ablative treatment comprising at least two optical fibers, each of which is equipped: at a first end with a connector to a laser source and, in proximity to a second end with a device for constraining to a pervious needle, including a coding system that characterizes one fiber with respect to the other, allowing said fibers to be distinguished from one another; wherein said device for constraining the fiber to the needle comprises a through hole for said fiber and a first end constrainable to said needle and at least partially transparent portion, on which a graduated scale is marked, the fiber having a reference mark visible through said transparent portion, to adjust the position of the fiber with respect to the device for constraining the needle.

25. A kit as claimed in claim 1, further comprising at least two needles having characteristics differing from one another to distinguish one needle from the other.

26. A kit as claimed in claim 2, further comprising at least two needles having characteristics differing from one another to distinguish one needle from the other.

27. A kit as claimed in claim 3, further comprising at least two needles having characteristics differing from one another to distinguish one needle from the other.

* * * * *